(12) United States Patent
Reidenberg et al.

(10) Patent No.: US 12,053,478 B2
(45) Date of Patent: *Aug. 6, 2024

(54) TAURULTAM, TAURINAMIDE AND METHYLENE GLYCOL TREATMENT FOR MYC—EXPRESSING TUMORS IN MAMMALIAN BODIES

(71) Applicant: CorMedix Inc., Berkeley Heights, NJ (US)

(72) Inventors: Bruce Reidenberg, Rye, NY (US); Robert DiLuccio, Viera, FL (US)

(73) Assignee: CorMedix Inc., Berkeley Heights, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/560,453

(22) Filed: Dec. 23, 2021

(65) Prior Publication Data

US 2022/0323451 A1 Oct. 13, 2022

Related U.S. Application Data

(63) Continuation of application No. 16/558,496, filed on Sep. 3, 2019, now abandoned, which is a continuation-in-part of application No. 15/403,876, filed on Jan. 11, 2017, now abandoned.

(60) Provisional application No. 62/277,243, filed on Jan. 11, 2016, provisional application No. 62/725,650, filed on Aug. 31, 2018.

(51) Int. Cl.
*A61K 31/549* (2006.01)
*A61K 9/16* (2006.01)
*A61K 31/047* (2006.01)
*A61K 31/132* (2006.01)
*A61K 45/06* (2006.01)

(52) U.S. Cl.
CPC ............ *A61K 31/549* (2013.01); *A61K 9/167* (2013.01); *A61K 31/047* (2013.01); *A61K 31/132* (2013.01); *A61K 45/06* (2013.01)

(58) Field of Classification Search
CPC .... A61K 31/549; A61K 9/167; A61K 31/047; A61K 31/132; A61K 45/06
See application file for complete search history.

(56) References Cited

U.S. PATENT DOCUMENTS

| | | | |
|---|---|---|---|
| 5,593,665 A | 1/1997 | Pfirrmann et al. | |
| 5,602,150 A | 2/1997 | Lidsky | |
| 6,479,481 B1 | 11/2002 | Stendel et al. | |
| 6,521,616 B2 | 2/2003 | Calabresi et al. | |
| 7,638,511 B2 * | 12/2009 | Stendel | A61K 31/54 514/222.5 |
| 7,928,102 B2 | 4/2011 | Redmond et al. | |
| 8,202,860 B2 | 6/2012 | Stendel et al. | |
| 9,012,444 B2 | 4/2015 | Redmond et al. | |
| 9,844,555 B2 | 12/2017 | Pfirrmann | |
| 2002/0049200 A1 | 4/2002 | Calabresi et al. | |
| 2002/0091123 A1 | 7/2002 | Redmond et al. | |
| 2002/0111345 A1 | 8/2002 | Calabresi et al. | |
| 2003/0027818 A1 | 2/2003 | Redmond et al. | |
| 2003/0044911 A1 | 3/2003 | Lerman | |
| 2003/0078257 A1 | 4/2003 | Calabresi et al. | |
| 2003/0092707 A1 | 5/2003 | Redmond et al. | |
| 2004/0176360 A1 | 9/2004 | Calabresi et al. | |
| 2005/0096314 A1 | 5/2005 | Pfirrmann | |
| 2005/0119254 A1 | 6/2005 | Pfirrmann | |
| 2008/0171738 A1 | 7/2008 | Redmond et al. | |
| 2008/0177217 A1 | 7/2008 | Polaschegg | |
| 2013/0085469 A1 | 4/2013 | Polaschegg | |
| 2013/0089606 A1 | 4/2013 | Pfirrmann et al. | |
| 2014/0140931 A1 | 5/2014 | Yu | |
| 2017/0056561 A1 | 3/2017 | DiLuccio et al. | |
| 2017/0196875 A1 | 7/2017 | DiLuccio | |
| 2018/0185378 A1 | 7/2018 | DiLuccio | |
| 2019/0381058 A1 | 12/2019 | Reidenberg et al. | |
| 2019/0381059 A1 | 12/2019 | Reidenberg et al. | |

FOREIGN PATENT DOCUMENTS

| | | |
|---|---|---|
| DE | 102010010360 | 9/2011 |
| EP | 1066830 | 1/2001 |
| JP | 2002-326936 | 11/2002 |
| JP | 2022-78296 | 5/2022 |
| RU | 2282438 C1 * | 8/2006 |
| WO | WO 91/13628 | 9/1991 |
| WO | WO 01/39762 | 6/2001 |
| WO | WO 01/039763 | 6/2001 |
| WO | WO 2002/097045 | 12/2002 |

(Continued)

OTHER PUBLICATIONS

Niemas-Teshiba et al. (Oncotarget. Jan. 19, 2018; 9(5): 6416-6432) (Year: 2018).*
Ackermann, R. et al. c-myc in bladder cancer Urol. Res., 1997, 25 (Suppl. 1), S45-S49 (Year: 1997).*
Angerer et al., Opinion on methylene glycol, Jun. 2012, pp. 1-14.
Cohn, The International Neuroblastoma Risk Group (INRG) Classification System: An INRG Task Force Report, Journal of Clinical Oncology, vol. 27, No. 2, Jan. 10, 2009.

(Continued)

*Primary Examiner* — Erin E Hirt
(74) *Attorney, Agent, or Firm* — Pandiscio & Pandiscio

(57) ABSTRACT

A method for treating a cancer which overexpresses any of N-myc genes, C-myc genes and/or L-myc genes in a mammalian body, the method comprising:

administering a composition to the mammalian body, wherein the composition comprises at least one from the group consisting of taurolidine; taurultam; taurinamide; methylene glycol; taurultam and taurinamide in a ratio of 1 taurultam:7 taurinamide; and taurultam, taurinamide and methylene glycol in a ratio of 1 taurultam:7 taurinamide:1 methylene glycol.

10 Claims, 11 Drawing Sheets

(56) References Cited

FOREIGN PATENT DOCUMENTS

| WO | WO 03/051902 | 6/2003 |
|---|---|---|
| WO | WO 2005/115357 | 12/2005 |
| WO | WO 2007/020509 | 2/2007 |
| WO | WO 2007/077528 | 7/2007 |
| WO | WO 2007/100883 | 9/2007 |
| WO | WO 2010/068654 | 6/2010 |
| WO | WO 2011/053562 | 5/2011 |
| WO | WO 2011/151722 | 12/2011 |
| WO | WO 2013/016696 | 1/2013 |
| WO | WO 2017/123635 | 7/2017 |
| WO | WO 2017/158570 | 9/2017 |

OTHER PUBLICATIONS

Dhar et al., Detouring of cisplatin to access mitochondrial genome for overcoming resistance, PNAS, vol. 111, No. 29, Jul. 22, 2014, pp. 10444-10449.
Donati et al., MYC and therapy resistance in cancer: risks and opportunities, Molecular Oncology, 2022, pp. 3828-3854.
Gabay et al., MYC Activation is a Hallmark of Cancer Initiation and Maintenance, 2014.
Jiang et al., The Connections Between Neural Crest Development and Neuroblastoma, Curr Top Dev Biol., 2011, pp. 77-127.
Jones et al., A study of the stability of taurolidine in plasma and protein-free serum, International Journal of Pharmaceutics, vol. 64, 1990, pp. R1-R4.
Kushner et al., Irinotecan Plus Temozolomide for Relapsed or Refractory Neuroblastoma, Journal of Clinical Oncology, vol. 24, No. 33, Nov. 20, 2006, pp. 5272-5275.
Llombart et al., Therapeutic targeting of "undruggable" MYC, Jan. 2022.
Luo et al., Association between Six Environmental Chemicals and Lung Cancer Incidence in the United States, Journal of Environmental and Public Health, vol. 2011, No. 9, Jan. 2011, pp. 1-9.
Rubie et al., Localised and Unresectable Neuroblastoma in Infants: Excellent Outcome With Primary Chemotherapy, Medical and Pediatric Oncology, 2001, pp. 247-250.
Stanford Medicine Children's Health, Neuroblastoma, Jul. 12, 2023.
Aceto, N. et al., Taurolidine and oxidative stress: a rationale for local treatment of mesothelioma, European Respiratory Journal, 2009, vol. 34, No. 6, pp. 1399-1407.
American Cancer Society, What is Neuroblastoma?, 2018 https://www.cancer.org/cancer/neuroblastoma/about/what-is-neuroblastoma.html.
Arcangeli, A. et al., "Novel perspectives in cancer therapy: Targeting ion channels" Drug Resistance Updates, 2015, 21-22: 11-19.
Bagci, O. et al., Amplification of Cellular Oncogenes in Solid Tumors, N Am J Med Sci., 2015, vol. 7, No. 8, pp. 341-346.
Baker D.L. et al., Outcome After Reduced Chemotherapy for Intermediate-Risk Neuroblastoma, New England Journal of Medicine, Sep. 30, 2010, vol. 363, No. 14, pp. 1313-1323.
Baker, D.L. et al., A Phase III Trial of Biologically-Based Therapy Reduction for Intermediate Risk Neuroblastoma, Abstract, Journal of Clinical Oncology, 2016, vol. 25, No. 18 Supplement.
Berthold F. et al., Myeloablative Megatherapy with Autologous Stem-Cell Rescue Versus Oral Maintenance Chemotherapy as Consolidation Treatment in Patients with High-Risk Neuroblastoma: A Randomised Controlled Trial, The Lancet Oncology, Sep. 2005, vol. 6, pp. 649-658.
Boyer, I. J. et al., Formaldehyde and Methylene Glycol, Oct. 12, 2011, pp. 1-41.
Braumann C. et al., Influence of Intraperitoneal and Systemic Application of Taurolidine and Taurolidine/Heparin During Laparoscopy on Intraperitoneal and Subcutaneous Tumor Growth in Rats, Clinical & Experimental Metastasis, 2001, vol. 18, pp. 547-552.
Braumann C. et al., Local and Systemic Chemotherapy with Taurolidine and Taurolidine/Heparin in Colon Cancer-Bearing Rats Undergoing Laparotomy, Clinical & Experimental Metastasis, 2003, vol. 20, pp. 387-394.
Braumann C. et al., Taurolidine reduces the tumor stimulating cytokine interleukin-1 beta in patients with resectable gastrointestinal cancer: a multicentre prosepective randomized trial, World Journal of Surgical Oncology, 2009, vol. 7, p. 30.
Brodeur G.M. et al., Amplification of N-myc in Untreated Human Neuroblastomas Correlates with Advanced Disease Stage, SCIENCE, Jun. 8, 1984, vol. 224, pp. 1121-1124.
Brodeur, Neuroblastoma: Biological Insights Into a Clinical Enigma, Nature Reviews Cancer, vol. 3, 2003, pp. 203-216.
Calabresi, P. et al., Taurolidine: Cytotoxic and Mechanistic Evaluation of a Novel Antineoplastic Agent, Cancer Research, 2001, vol. 61, pp. 6816-6821.
Chromik A.M. et al., Synergistic Effects in Apoptosis Induction by Taurolidine and TRAIL in HCT-15 Colon Carcinoma Cells, Journal of Investigative Surgery, 2007, vol. 20, pp. 339-348.
Clinical trial No. NCT00410631, Observation, Combination Chemotherapy, Radiation Therapy, and/or Autologous Stem Cell Transplant in Treating Young Patients with Neuroblastoma, https://clinicaltrials.gov/ct2/show/NCT00410631.
Clinical trial No. NCT01 I 75356, Induction Therapy Including 131 I-MIBG and Chemotherapy in Treating Patients with Newly Diagnosed High-Risk Neuroblastoma Undergoing Stem Cell Transplant, Radiation Therapy, and Maintenance Therapy with Isotretinoin, https://clinicaltrials.gov/ct2/show/NCT01175356.
CorMedix press release, Cormedix Inc. Announces Agreement With Nanoproteagen for Its Proprietary Nanoparticle Technology, Nanopro™, in Combination With CRMD-005 for Pediatric Neuroblastoma, 2016.
Cosmetic Ingredient Review, Formaldehyde and Methylene Glycol, 2011.
Daigeler A. et al., Synergistic Apoptotic Effects of Taurolidine and TRAIL on Squamous Carcinoma Cells of the Esophagus, International Journal of Oncology, 2008, vol. 32, pp. 1205-1220.
DeCroes, O. G. "Development of poly(lactic acid)-poly(ethylene glycol) nanoparticles for the delivery . . . " Clemson University Press, M.S. Thesis, Aug. 2014.
Diskin S.J. et al., Copy Number Variation at Iq21.I Associated with Neuroblastoma, Nature, Jun. 18, 2009, vol. 459, No. 7249, pp. 987-991.
Eschenburg et al., "Taurolidine cooperates with antineoplastic drugs in neuroblastoma cells", Genes & Cancer, 2014, 5: 460-469.
Fangyuan et al. "Progress in the study of poly (lactide-co-glycolide) nanoparticles for anticancer agents delivery", Northwest Pharmaceutical Journal, 2013, vol. 28, No. 6, pp. 656-660.
Farrington, M., Chemotherapy of Infections, Clinical Pharmacology, 2012.
FDA Guidance for Industry, Estimating the Maximum Safe Starting Dose in Initial Clinical Trials for Therapeutics in Adult Healthy Volunteers, 2005.
George R.E. et al., High-Risk Neuroblastoma Treated with Tandem Autologous Peripheral-Blood Stem Cell-Supported Transplantation: Long-Term Survival Update, Journal of Clinical Oncology, Jun. 20, 2006, vol. 24, No. 18, pp. 2891-2896.
Gisselsson D. et al., Distinct Evolutionary Mechanisms for Genomic Imbalances in High-Risk and Low-Risk Neuroblastomas, Journal of Carcinogenesis, Sep. 26, 2007, vol. 6, No. 15, pp. 1-8.
Gong et al. "The pharmacokinetics of taurolidine metabolites in healthy volunteers", J Clin Pharmacol, 2007, 47: 697-703.
Hato et al. (Clin. Cancer Res., 2014, 20, 2831-2837). (Year: 2014).
Harati et al., "TRAIL and Taurolidine Enhance the Anticancer Activity of Doxorubicin, Trabectedin and Mafosfamide in HT1080 Human Fibrosarcoma Cells", Anticancer Res, 2012, 32: 2967-2984.
Karlisch C. et al., Effects of TRAIL and Taurolidine on Apoptosis and Proliferation in Human Rhabdomyosarcoma, Leiomyosarcoma and Epithelioid Cell Sarcoma, International Journal of Oncology, 2013, vol. 42, pp. 945-956.
Kohane, D.S. et al., Microparticles and Nanoparticles for Drug Delivery, Biotechnology and Bioengineering, Dec. 28, 2006, vol. 96, No. 2, pp. 203-209.
Kreissman, S.G. et al., Response and Toxicity to a Dose-Intensive Multi-Agent Chemotherapy Induction Regimen for High Risk

(56) References Cited

OTHER PUBLICATIONS

Neuroblastoma (HR-NB): A Children's Oncology Group (COG A3973) Study, Abstract, Journal of Clinical Oncology, 2016, vol. 25, No. 18 Supplement.

Kushner B.H. et al., Irinotecan Plus Temozolomide for Relapsed or Refractory Neuroblastoma, Journal of Clinical Oncology, Nov. 20, 2006, vol. 24, No. 33, pp. 5271-5276.

Ladenstein R. et al., Randomized Trail of Prophylactic Granulocyte Colony-Stimulating Factor During Rapid COJEC Induction in Pediatric Patients with High-Risk Neuroblastoma: The European HR-NBLI/SIOPEN Study, Jul. 20, 2010, vol. 28, No. 21, pp. 3516-3524.

Luckert, C. et al., Taurolidine Specifically Inhibits Growth of Neuroblastoma Cell Lines In Vitro, Journal of Pediatric Hematology/Oncology, 2014, vol. 36, No. 4, pp. e219-e223.

Ma, L.; Kohli, M.; Smith, A. "Nanoparticles for Combination Drug Therapy" ACS Nano, 2013, 7(11), 9518-9525.

Maris, Recent Advances in Neuroblastoma, New England Journal of Medicine, 2010, pp. 2202-2211.

Marley, K. et al., Pharmacokinetic study and evaluation of the safety of taurolidine for dogs with osteosarcoma, Journal of Experimental & Clinical Cancer Research, Oct. 11, 2013, vol. 32, No. 74, pp. 1-24.

Martinotti S. et al., In Vitro Screening of Synergistic Ascorbate-Drug Combinations for the Treatment of Malignant Mesothelioma, Toxicology in Vitro, 2011, vol. 25, pp. 1568-1574.

Matthay K.K. et al., Long-Term Results for Children with High-Risk Neuroablastoma Treated on a Randomized Trial of Myeloablative Therapy Followed by 13-cis-Retinoic Acid: A Children's Oncology Group Study, Journal of Clinical Oncology, Mar. 1, 2009, vol. 27, No. 7, pp. 1007-1013.

Matthay, K. K. "Neuroblastoma: biology and therapy" Oncology, 1997, 11 (12), 1857-1866 (abstract only).

Mayo Clinic, Neuroblastoma, 2020, https://www.mayoclinic.org/diseases-conditions/neuroblastoma/symptoms-causes/syc-20351017.

McCall E.E. et al., Maternal Hair Dye Use and Risk of Neuroblastoma in Offspring, Cancer Causes and Control, 2005, vol. 16., pp. 743-748.

Menegaux F. et al., Day Care, Childhood Infections, and Risk of Neuroblastoma, American Journal of Epidemiology, 2004, vol. 159, No. 9, pp. 843-851.

Mishra et al. Primary Pediatric Intracranial Neuroblastoma: A Report of Two Cases, Jounral of Pediatric Neurosciences, vol. 13, No. 3, 2018, pp. 366-370.

Monson et al. "Taurolidine inhibits tumor necrosis factor (TNF) toxicity—new evidence of TNF and endotoxin synergy", Eur J Surg Oncol, Jun. 1993, vol. 19, No. 3, pp. 226-231.

Mudshinge, S. R. et al. "Nanoparticles: emerging carriers for drug delivery" Saudi Pharmaceutical Journal, 2011, 19, 129-141.

NANT home page, 2017, http://www.nant.org.

Neary et al., "The Evolving Role of Taurolidine in Cancer Therapy", Ann Sur Oneal, 2010, 17: 1135-1143.

Olshan A.F. et al., Hormone and Fertility Drug Use and the Risk of Neuroblastoma: A Report from the Children's Cancer Group and the Pediatric Oncology Group, American Journal of Epidemiology, 1999, vol. 150, No. 9, pp. 930-938.

Patil, Y. et al., Nanoparticle-mediated simultaneous and targeted delivery of paclitaxel and tariquidar overcomes tumor drug resistance, Journal of Controlled Release, 2009, vol. 136, pp. 21-29.

Pearson A. D.J. et al., High-Dose Rapid and Standard Induction Chemotherapy for Patients Aged Over 1 Year with Stage 4 Neuroblastoma: A Randomised Trial, The Lancet Oncology, 2008, vol. 9, pp. 247-256.

Plantone et al., "Neurological disease associated with autoantibodies targeting the voltage-gated potassium channel complex: immunobiology and clinical characteristics", Neuroimmunol Neuroinflammation, 2016, 3: 69-78.

Principles of Manual Medicine (Feb. 19, 2015, hllp://web.archive.org/web/20150219091248/hllp://hal.bim.msu.edu:80/cmeonline/Autonomic/start.html) (Year: 2015).

Pritchard J et al., High Dose Melphalan in the Treatment of Advanced Neuroblastoma: Results of a Randomised Trial (ENSG-1) by the European Neuroblastoma Study Group, Pediatric Blood & Cancer, 2005, vol. 44, pp. 348-357.

Rasenack et al., Micron-size drug particles: common and novel micronization techniques, 2004, vol. 9, No. 1.

Reidenberg B et al., Multi-Resistant Candida auris is Susceptible to Taurlidine, Aspergillus & Aspergillosis, 2017.

Reidenberg, B. E. et al., Postmarketing experience with Neutrolin (taurolidine, heparin, calcium citrate) catheter lock solution in hemodialysis patients, European Journal of Clinical Microbiology & Infectious Diseases, Dec. 6, 2017, vol. 37, pp. 661-663.

Simon et al., J. Cancer Res. Clin. Oneal., 2007, 133, 653-661.

Stendel, R. et al., Enhancement of Fas-Ligand-Mediated Programmed Cell Death by Taurolidine, Abstract, Anticancer Research, 2003, vol. 23.

Strenger V. et al., Diagnostic and Prognostic Impact of Urinary Catecholamines in Neuroblastoma Patients, Pediatric Blood & Cancer, 2007, vol. 48, pp. 504-509.

Swift, L. et al., Dual functionality of the antimicrobial agent taurolidine which demonstrates effective anti-tumor properties in pediatric neuroblastoma, Investigational New Drugs, Jul. 2, 2019.

Tansey, W.P., Mammalian MYC Proteins and Cancer, New Journal of Science, 2014.

Tivnan et al., Inhibition of Neuroblastoma Tumor Growth by Targeted Delivery of MicroRNA-34a Using Anti-Disialoganglioside GD2 Coated Nanoparticles, PloS ONE, vol. 7, No. 5, 2012.

Tsuda, H. et al., Retrospective study on amplification of N-myc and c-myc genes in pediatric solid tumors and its association with prognosis and tumor differentiation, Abstract, Lab Invest. 1988, vol. 59, No. 3, pp. 321-327.

Veronese et al., PEGylation, successful approach to drug delivery, DDT, vol. 10, No. 21, 2005, pp. 1451-1458.

Wagner et al., Targeting Methylguanine-DNA Methyltransferase in the Treatment of Neuroblastoma, Clinical Cancer Research, vol. 13, No. 18, 2007, pp. 5418-5425.

Wang K. et al., Integrative Genomics Identifies LMO1 as a Neuroblastoma Oncogene, Nature, Jan. 13, 2011, vol. 469, No. 7329, pp. 216-220.

Wickstrom et al., Wnt/β-catenin pathway regulates MGMT gene expression in cancer and inhibition of Wnt signaling prevents chemoresistance, Nature Communications, 2015.

Wohlfart et al., "Efficient Chemotherapy of Rat Glioblastoma using Doxorubicin-loaded PLGA Nanoparticles with Different Stabilizers", PloS ONE, 2011, 6: e19121.

Wong et al., "The cytotoxic effects of lipidic formulated gold porphyrin nanoparticles for the treatment of neuroblastoma", Nanotechnology, Science and Applications, Jun. 17, 2010, pp. 23-28.

Wong, H.L. et al., Simultaneous delivery of doxorubicin and GG918 (Elacridar) by new Polymer-Lipid Hybrid Nanoparticles (PLN) for enhanced treatment of multidrug-resistant breast cancer, Journal of Controlled Release, 2006, vol. 116, pp. 275-284.

Zhu et al., Brain metastasis in children with stage 4 neuroblastoma after multidisciplinary treatment, Chinese Journal of Cancer, vol. 34, No. 49, 2015.

Buchholz et al., Effectivity and Toxicity of Taurultam (TRLT) as Anti-Neoplasticagent in Malignant Tumor Cells—In Vitro Study of Pancreatic and Colon Cancer Cell Lines, German Medical Science GMS Publishing House, Apr. 2013.

Mohler et al., Redox-directed cancer therapeutics: Taurolidine and Piperlongumine as broadly effective antineoplastic agents, International Journal of Oncology, vol. 45, 2014, pp. 1329-1336.

Stendel et al., Pharmacokinetics of Taurolidine following Repeated Intravenous Infusions Measured by HPLC-ESI-MS/MS of the Deriviates Taurullame and Taurinamide in Glioblastoma Patients, Clinical Pharmacokinetics, vol. 46, No. 6, 2007, pp. 513-524.

Lee et al. Synergistic anti-cancer effects via co-delivery of TNF-related apoptosis-inducing ligand (TRAIL/Apo2L) and doxorubicin using micellar nanoparticles, Mol. BioSyst., May 2011, vol. 7, No. 5, pp. 1512-1522.

Shi et al., Organic nanoscale drug carriers couple with ligands for targeted drug delivery in cancer, Journal of Materials Chemistry, Apr. 9, 2009, vol. 19, pp. 5484-5498.

(56) References Cited

OTHER PUBLICATIONS

Vita et al., The Myc oncoprotein as a therapeutic target for human cancer, Seminars in Cancer Biology, 2006, vol. 16, Issue 4, pp. 318-330.
Dinarvand et al., "Polylactide-co-glycolide nanoparticles for controlled delivery of anticancer agents", International Journal of Nanomedicine, 2011, vol. 6, pp. 877-895.

* cited by examiner

Note: percent survival is percent survival of the animal (not the tumor).

Note: percent survival is percent survival of the animal (not the tumor).

Mean Pharmacokinetic Parameters of Taurultam

| Duration of infusion hr | n | $AUC_{(0-24)}$ hr*µg/mL | $AUC_{(0-\infty)}$ hr*µg/mL | $C_{max}$ µg/mL | half life hr | $T_{max}$ hr |
|---|---|---|---|---|---|---|
| 2 | 6 | 34.9 ± 9.6 | 35.7 ± 9.0 | 16.0 ± 4.5 | 1.1 ± 0.3 | 1.50 |
| 1 | 5 | 37.3 ± 10.1 | 40.7 ± 11.2 | 32.0 ± 16.1 | 1.2 ± 0.7 | 0.75 |
| 0.5 | 6 | 44.8 ± 9.8 | 51.8 ± 10.6 | 51.4 ± 12.2 | 2.1 ± 1.1 | 0.50 |
| All Groups | | 38.8 ± 9.8 | 42.9 ± 11.4 | 32.0 ± 17.9 | 1.5 ± 0.9 | 0.50* |

All data are presented as mean ± S.D.
* = median

FIG. 11

Mean Pharmacokinetic Parameters of Taurinamide

| Duration of infusion hr | n | $AUC_{(0-24)}$ hr*µg/mL | $AUC_{(0-\infty)}$ hr*µg/mL | $C_{max}$ µg/mL | half life hr | $T_{max}$ hr |
|---|---|---|---|---|---|---|
| 2 | 6 | 315.4 ± 46.5 | 356.5 ± 61.1 | 53.9 ± 10.8 | 6.9 ± 1.5 | 2.00 |
| 1 | 5 | 233.9 ± 29.4 | 260.0 ± 35.3 | 59.4 ± 19.4 | 6.5 ± 1.4 | 1.00 |
| 0.5 | 6 | 271.7 ± 61.4 | 310.3 ± 67.2 | 62.6 ± 16.8 | 6.7 ± 1.2 | 0.63 |
| All Groups | | 273.4 ± 55.8 | 312.7 ± 63.2 | 57.3 ± 15.3 | 6.7 ± 1.3 | 1.00* |

All data are presented as mean ± S.D.
* = median

FIG. 12

TAURULTAM, TAURINAMIDE AND METHYLENE GLYCOL TREATMENT FOR MYC—EXPRESSING TUMORS IN MAMMALIAN BODIES

REFERENCE TO PENDING PRIOR PATENT APPLICATIONS

This patent application is a continuation of prior U.S. patent application Ser. No. 16/558,496, filed Sep. 3, 2019 by CorMedix Inc. for TAUROLIDINE TREATMENT FOR MYC-EXPRESSING TUMORS IN MAMMALIAN BODIES, which patent application in turn:

(i) is a continuation-in-part of prior U.S. patent application Ser. No. 15/403,876, filed Jan. 11, 2017 by CorMedix Inc. and Robert DiLuccio for THERAPEUTIC NANOPARTICLES FOR THE TREATMENT OF NEUROBLASTOMA AND OTHER CANCERS, which patent application claims benefit of prior U.S. Provisional Patent Application Ser. No. 62/277,243, filed Jan. 11, 2016 by CorMedix Inc. and Robert DiLuccio for NANOPARTICLE SYSTEM FOR THE TREATMENT OF NEUROBLASTOMA; and (ii) claims benefit of prior U.S. Provisional Patent Application Ser. No. 62/725,650, filed Aug. 31, 2018 by CorMedix Inc. and Bruce Reidenberg et al. for TAUROLIDINE TREATMENT FOR MYC-EXPRESSING TUMORS IN MAMMALIAN BODIES.

The four (4) above-identified patent applications are hereby incorporated herein by reference.

FIELD OF THE INVENTION

This invention relates to therapeutic methods and compositions in general, and more particularly to therapeutic methods and compositions for the treatment of MYC-expressing tumors in mammalian bodies.

BACKGROUND OF THE INVENTION

Taurolidine is a well known antimicrobial with a published mechanism of action and antimicrobial spectrum. Taurolidine is unstable in circulation and therefore has not been successfully developed for systemic infections. Taurolidine has demonstrated efficacy in local application for peritonitis and for prevention of infection when used as a catheter-lock solution.

Taurolidine has recently been investigated for oncolytic activity and found to have an inhibitory effect on cell lines in culture, in combination with standard chemotherapy or alone. Despite claims that in vitro inhibitory concentrations are clinically achievable, the only published human pharmacokinetic study showed NO measurable concentration of taurolidine in healthy volunteers when 5 grams of taurolidine were given intravenously by 20 minute infusion. This is believed to be due to the rapid hydrolysis of taurolidine when administered systemically in a mammalian body.

MYC oncogenes have been widely described in solid tumors and in lymphoma/leukemia.

Taurolidine has demonstrated efficacy in treating neuroblastoma in a laboratory cell line. This cell line is known to overexpress N-myc genes.

Taurolidine has demonstrated efficacy in treating ovarian cancer in a human ovarian cell tumor line implanted in mice. This cell line is known to overexpress C-myc genes.

Taurolidine has demonstrated efficacy in treating lung cancer in a laboratory cell line. This cell line is known to overexpress L-myc genes.

A need exists for a new method and composition which are effective against MYC-expressing tumors in mammalian bodies.

SUMMARY OF THE INVENTION

In accordance with the present invention, taurolidine, and/or the hydrolysis products of taurolidine, is/are used to treat tumors that overexpress N-myc genes, C-myc genes and/or L-myc genes in mammalian bodies. Examples of tumors that may overexpress N-myc genes, C-myc genes and/or L-myc genes include, but are not limited to, lymphoma, melanoma, multiple myeloma, neuroblastoma, colon, breast and lung cancers.

The preferred hydrolysis products of taurolidine may comprise at least one from the group consisting of:
- taurultam;
- taurinamide;
- methylene glycol;
- taurultam and taurinamide in a ratio of 1 taurultam:7 taurinamide; and
- taurultam, taurinamide and methylene glycol in a ratio of 1 taurultam:7 taurinamide:1 methylene glycol.

The taurolidine is given with a dosage range of from 5 mg/kg to 280 mg/kg, with optimal range between 5 mg/kg and 60 mg/kg, from once daily through weekly, for an effective period of time based on individual patient response.

The taurultam is given with a dosage range of from 5 mg/kg to 280 mg/kg, with optimal range between 5 mg/kg and 60 mg/kg, from once daily through weekly, for an effective period of time based on individual patient response.

The taurinamide is given with a dosage range of from 5 mg/kg to 280 mg/kg, with optimal range between 5 mg/kg and 60 mg/kg, from once daily through weekly, for an effective period of time based on individual patient response.

The methylene glycol is given with a dosage range of from 2.5 mg/kg to 160 mg/kg, with optimal range between 2.5 mg/kg and 30 mg/kg, from once daily through weekly, for an effective period of time based on individual patient response.

The taurultam and taurinamide (in a ratio of 1 taurultam:7 taurinamide) is given with a dosage range of taurultam from 5 mg/kg to 280 mg/kg, with optimal range between 5 mg/kg and 40 mg/kg, combined with taurinamide with a dosage range of from 5 mg/kg to 280 mg/kg, with optimal range from 35 mg/kg to 40 mg/kg, from once daily through weekly, for an effective period of time based on individual patient response.

The taurultam, taurinamide and methylene glycol (in a ratio of 1 taurultam:7 taurinamide:1 methylene glycol) is given with a dosage range of taurultam from 5 mg/kg to 280 mg/kg, with optimal range between 5 mg/kg and 40 mg/kg, combined with taurinamide with a dosage range of from 5 mg/kg to 280 mg/kg, with optimal range from 35 mg/kg to 40 mg/kg, further combined with methylene glycol with a dosage range of from 2.5 mg/kg to 160 mg/kg with optimal range from 5 mg/kg to 40 mg/kg, from once daily through weekly, for an effective period of time based on individual patient response.

The taurolidine, and/or the hydrolysis products of taurolidine, can be given systemically, preferably intramuscularly or intravenously.

In one preferred form of the invention, the taurolidine, and/or the hydrolysis products of taurolidine, is/are delivered systemically in a "shielded form" so that the taurolidine, or the hydrolysis products of taurolidine, can reach the site of the tumor without premature degradation, whereupon the taurolidine, or the hydrolysis products of taurolidine, can treat the tumor.

More particularly, in one preferred form of the invention, the taurolidine and/or the hydrolysis products of taurolidine can be delivered in the form of a nanoparticle, where the nanoparticle comprises a core of the taurolidine and/or the hydrolysis products of taurolidine and an exterior coating which is configured to prevent premature exposure of the taurolidine and/or the hydrolysis products of taurolidine prior to the arrival of the nanoparticle to the tumor site. The exterior coating breaks down as the nanoparticle travels from the site of the insertion to the site of the tumor so as to release the taurolidine and/or the hydrolysis products of taurolidine intact at the site of the tumor. In one preferred form of the invention, the coating comprises an absorbable polymer or lipid which breaks down as the nanoparticle travels from the site of insertion to the site of the tumor.

In another form of the invention, the taurolidine and/or the hydrolysis products of taurolidine (i.e., the active ingredient) may be delivered using a polymer system which is configured to delay premature degradation of the active ingredient. By way of example but not limitation, the taurolidine and/or the hydrolysis products of taurolidine may be "pegylated" using polyethylene glycols (PEGs) to delay premature degradation of the active ingredient.

The taurolidine, and/or the hydrolysis products of taurolidine, may be delivered as either a single agent or in combination with other oncolytic agents and/or radiotherapy.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 11 is a chart showing the mean pharmacokinetic parameters of taurultam; and FIG. 12 is a chart showing the mean pharmacokinetic parameters of taurinamide.

DETAILED DESCRIPTION OF THE INVENTION

Taurolidine was developed as an anti-infective, but has been found to have oncolytic activity against neuroblastoma tumors in a laboratory cell line. This laboratory cell line is known to overexpress N-myc genes. More particularly, taurolidine has been found to have surprising oncolytic activity in cell cultures of human cancer cells expressing N-myc, and now in a rodent cancer model based on an N-myc expressing human cancer cell line.

Figure 1:
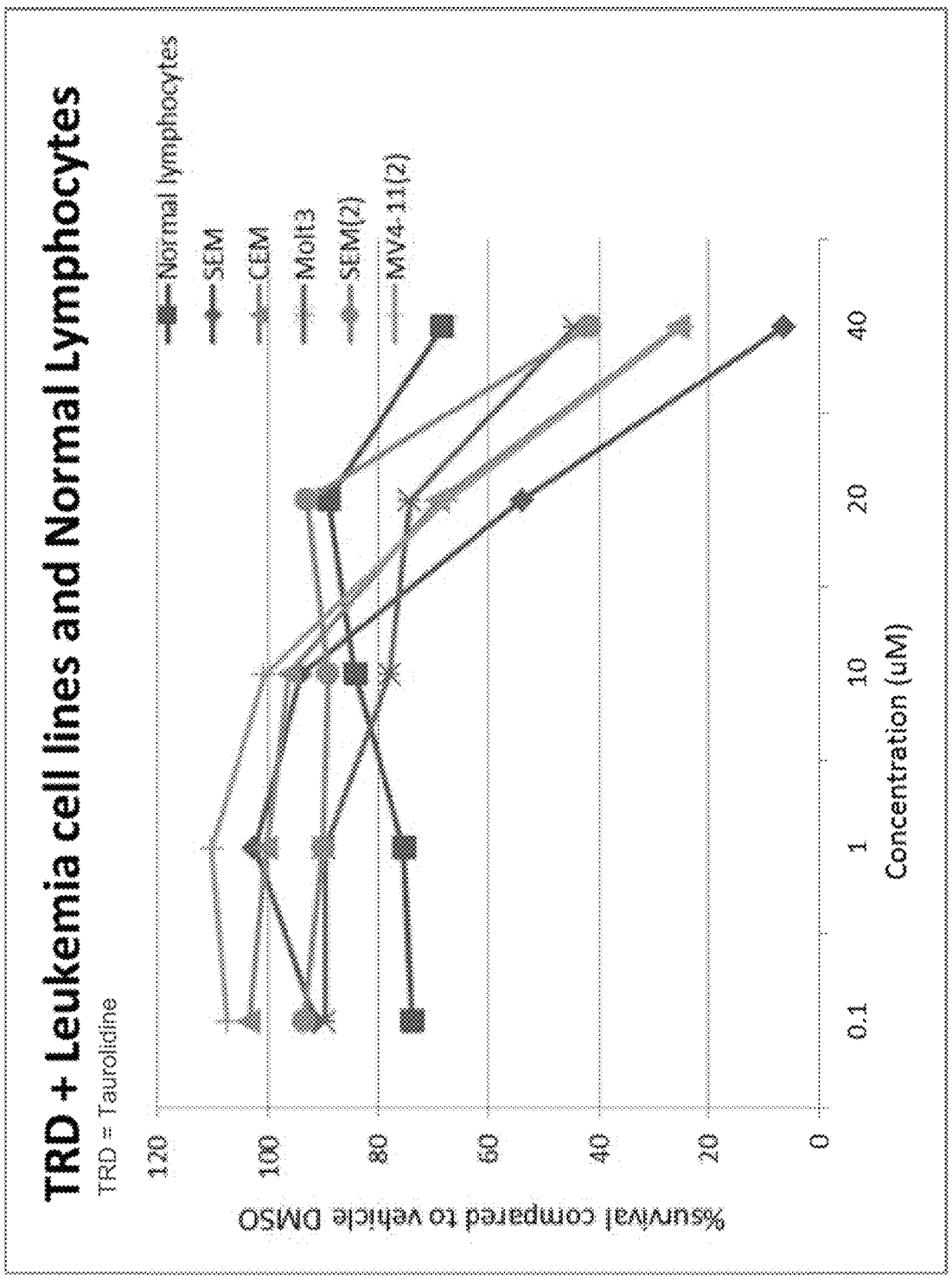
FIG. 1 is a graph showing that leukemia cell lines appear more sensitive to the effects of taurolidine compared to healthy lymphocytes in vitro (not in vivo)

It has been found that leukemia cell lines appear more sensitive to the effects of taurolidine compared to healthy lymphocytes in vitro (not in vivo). See FIG. 1.

Figure 2:
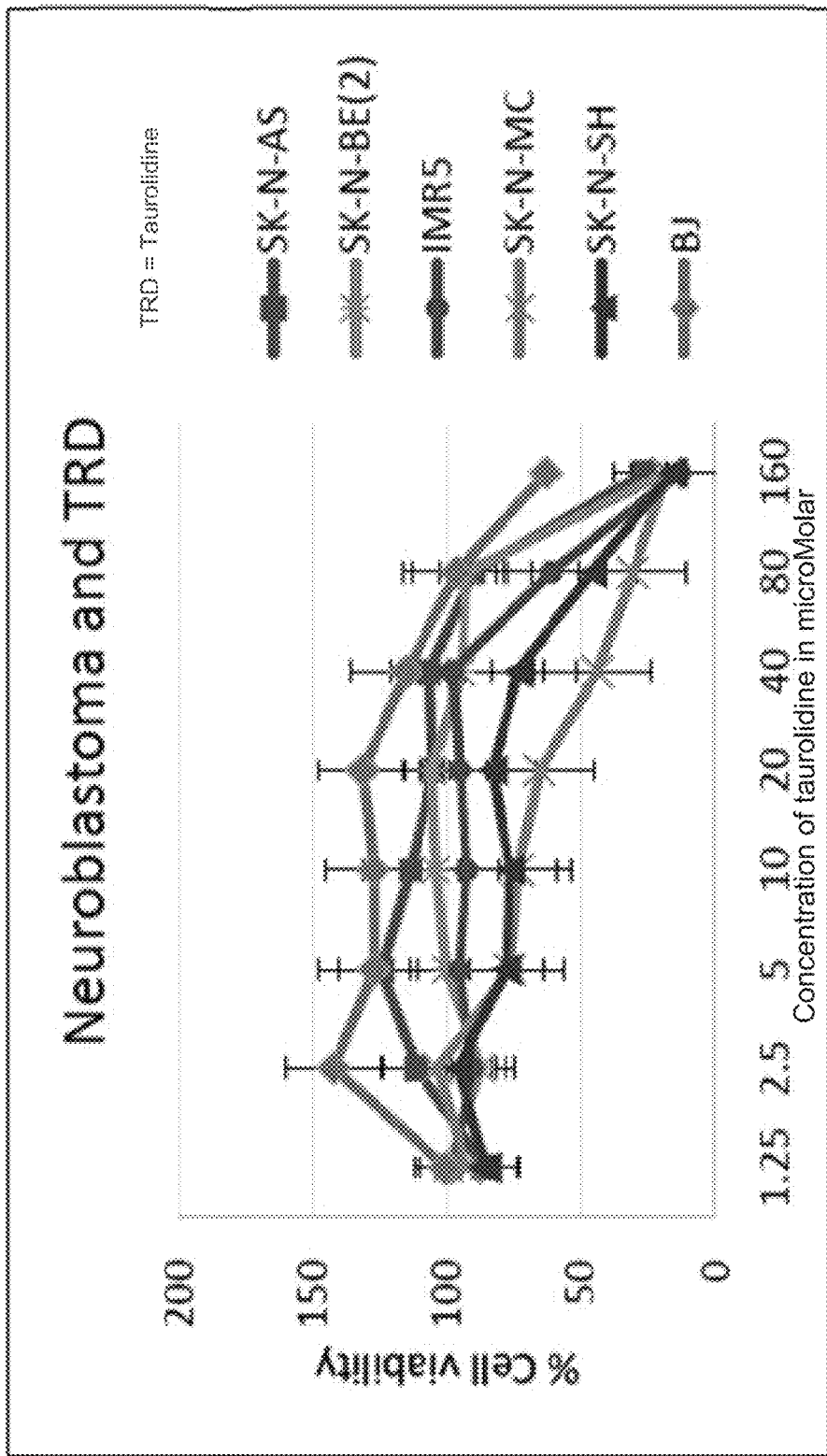
FIG. 2 is a graph showing that neuroblastoma cell lines are more sensitive to a decrease in viability due to taurolidine when compared to healthy fibroblasts (BJ on graph) in vitro (not in vivo)
Figure 3:
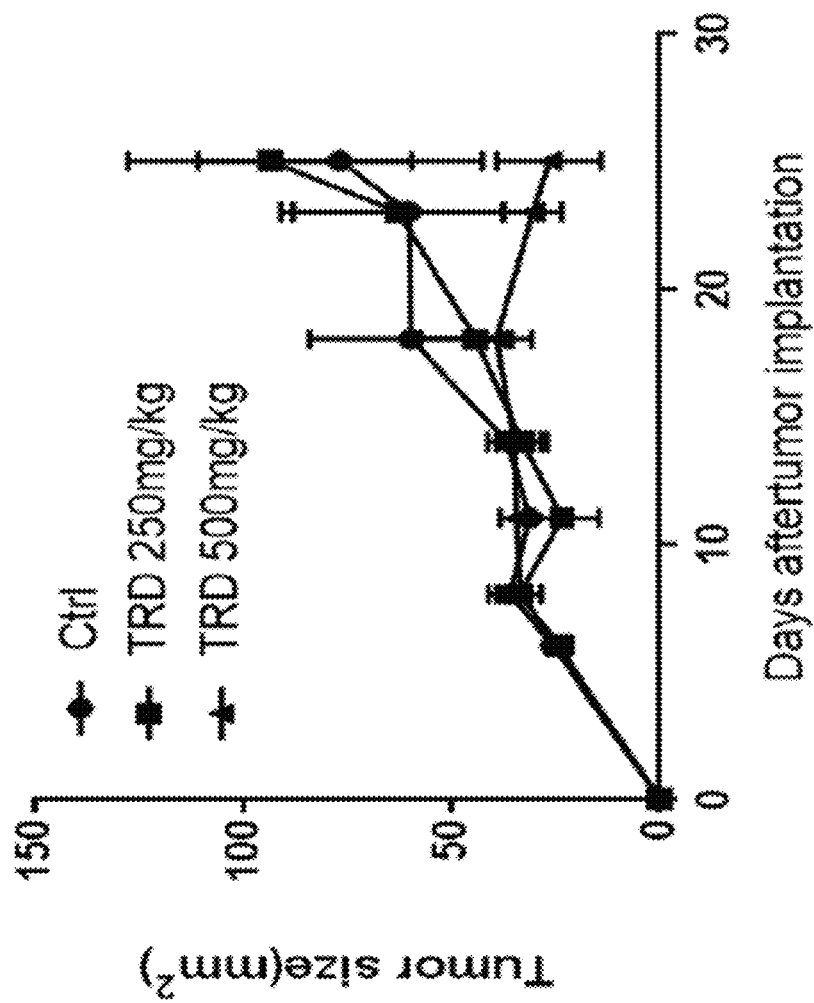
FIGS. 3-6 are graphs or photographs showing that taurolidine given to CB57 SCID mice with measurable tumors from a neuroblastoma cell line implanted subcutaneously in the CB57 SCID mice has efficacy in IMR5 tumors and measurable efficacy in SK-N-AS tumors in vivo (not in vitro)
Figure 4:
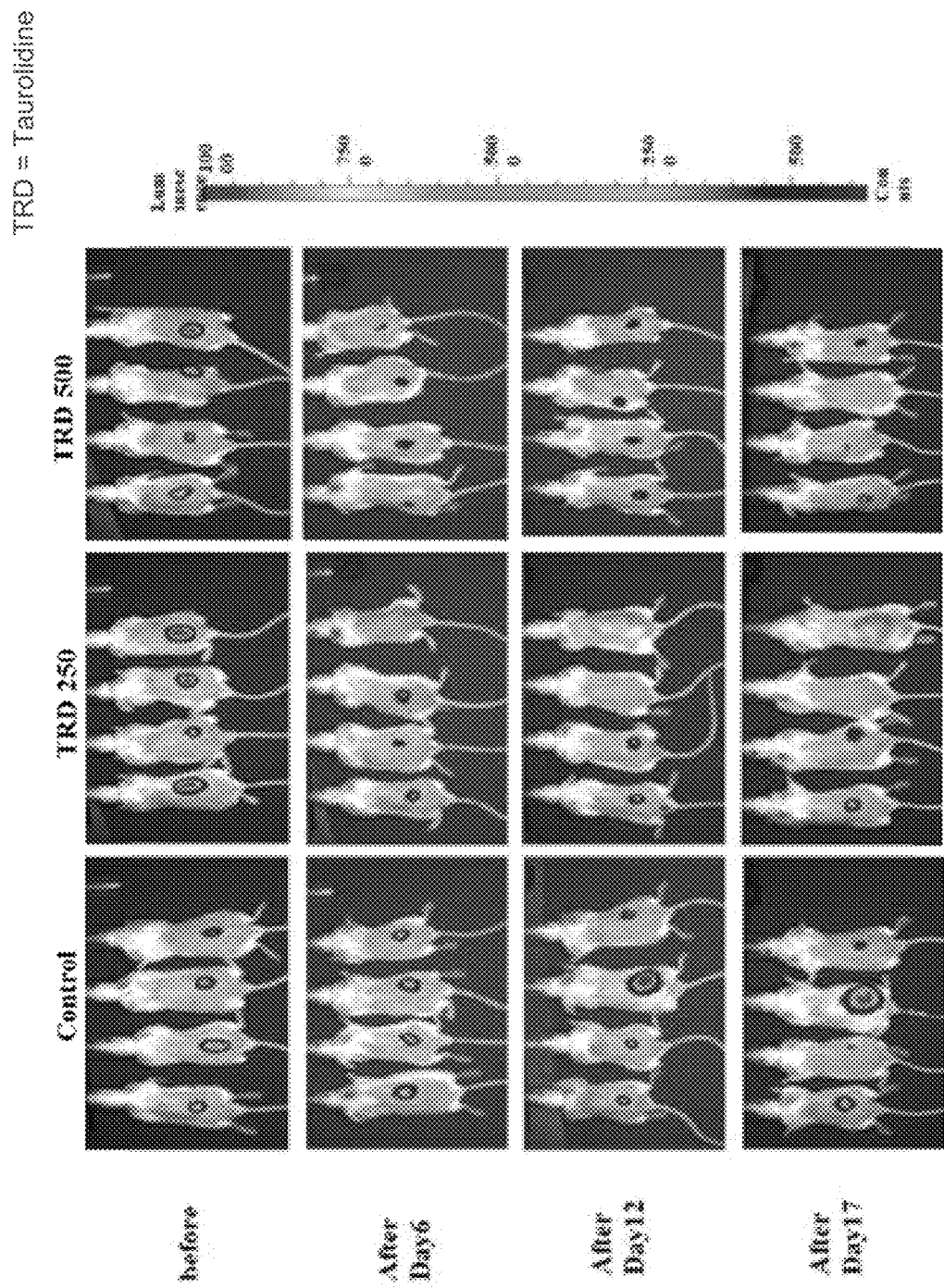
Figure 5:
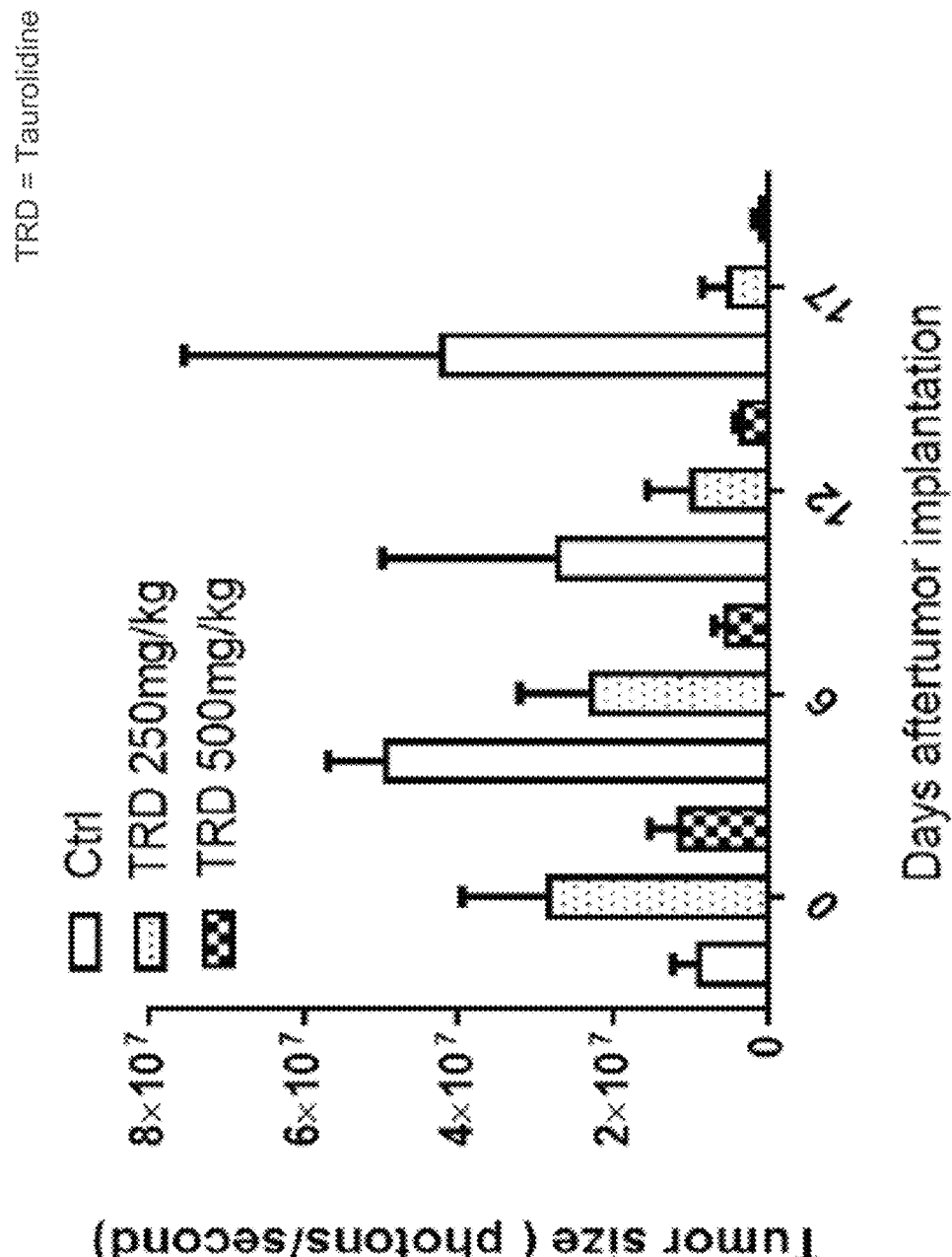
Figure 6:
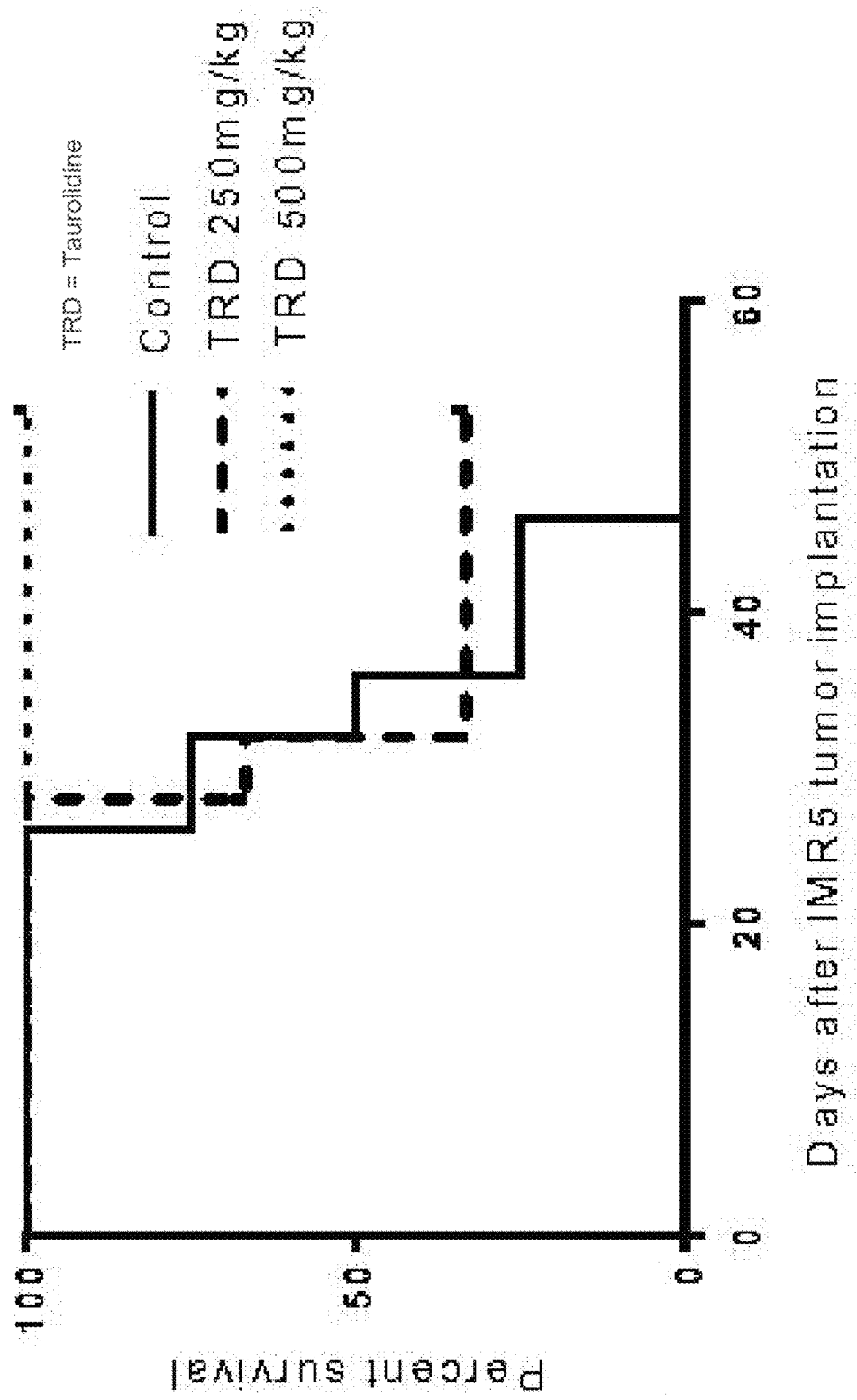

It has also been found that neuroblastoma cell lines are more sensitive to a decrease in viability due to taurolidine when compared to healthy fibroblasts in vitro (not in vivo). See FIG. 2.

Furthermore, taurolidine given to CB57 SCID mice with measurable tumors from a neuroblastoma cell line implanted subcutaneously in the CB57 SCID mice showed dramatic efficacy in IMR5 tumors and measurable efficacy in SK-N-AS tumors in vivo (not in vitro). See FIGS. 3-6.

Figure 7:
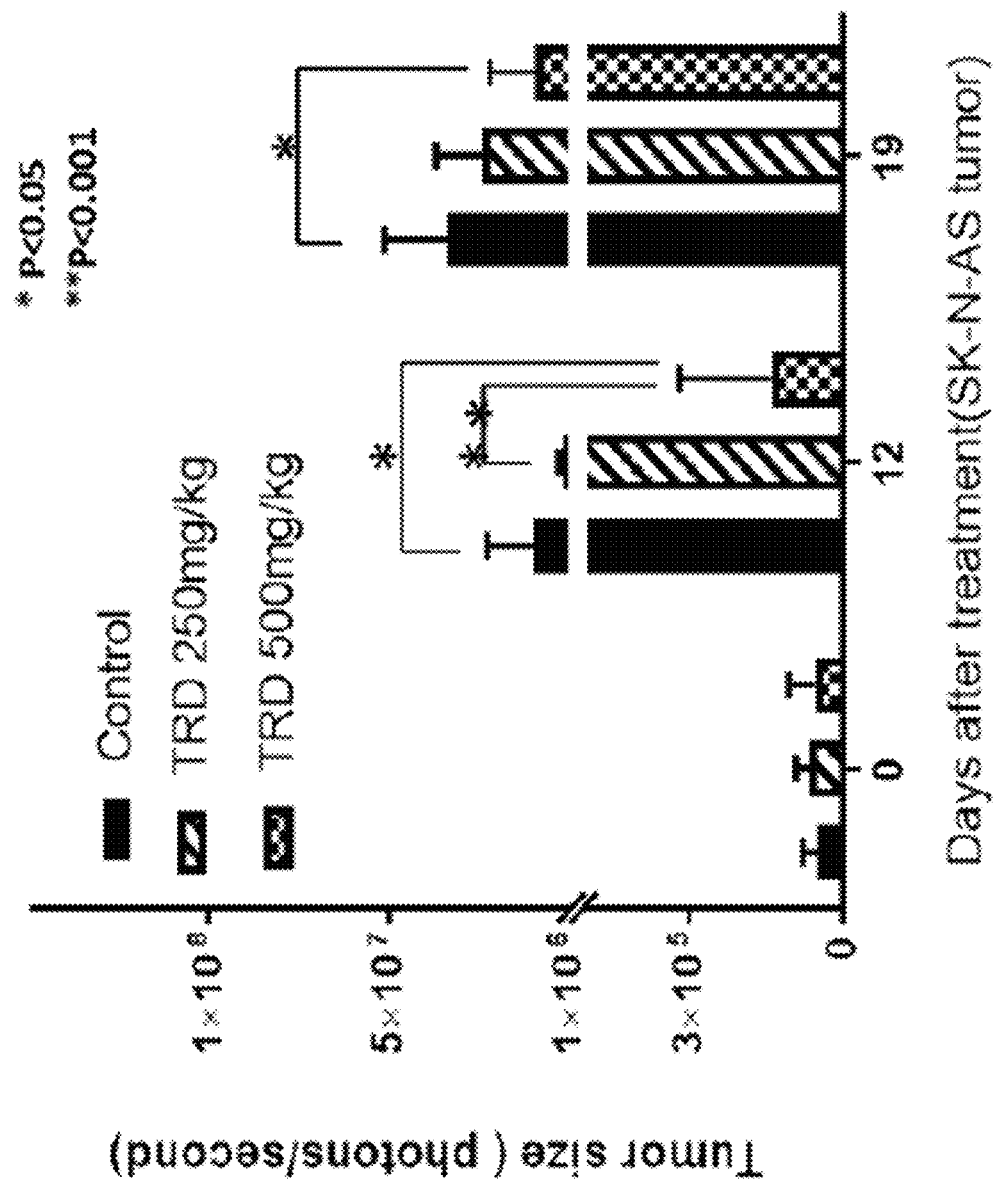
FIGS. 7 and 8 are graphs showing that statistically significant decreases in tumor size were achieved when taurolidine was administered to treat mice with a different cell line (SK-N-AS) also derived from neuroblastoma but overall survival was not significantly different from control.
Figure 8:
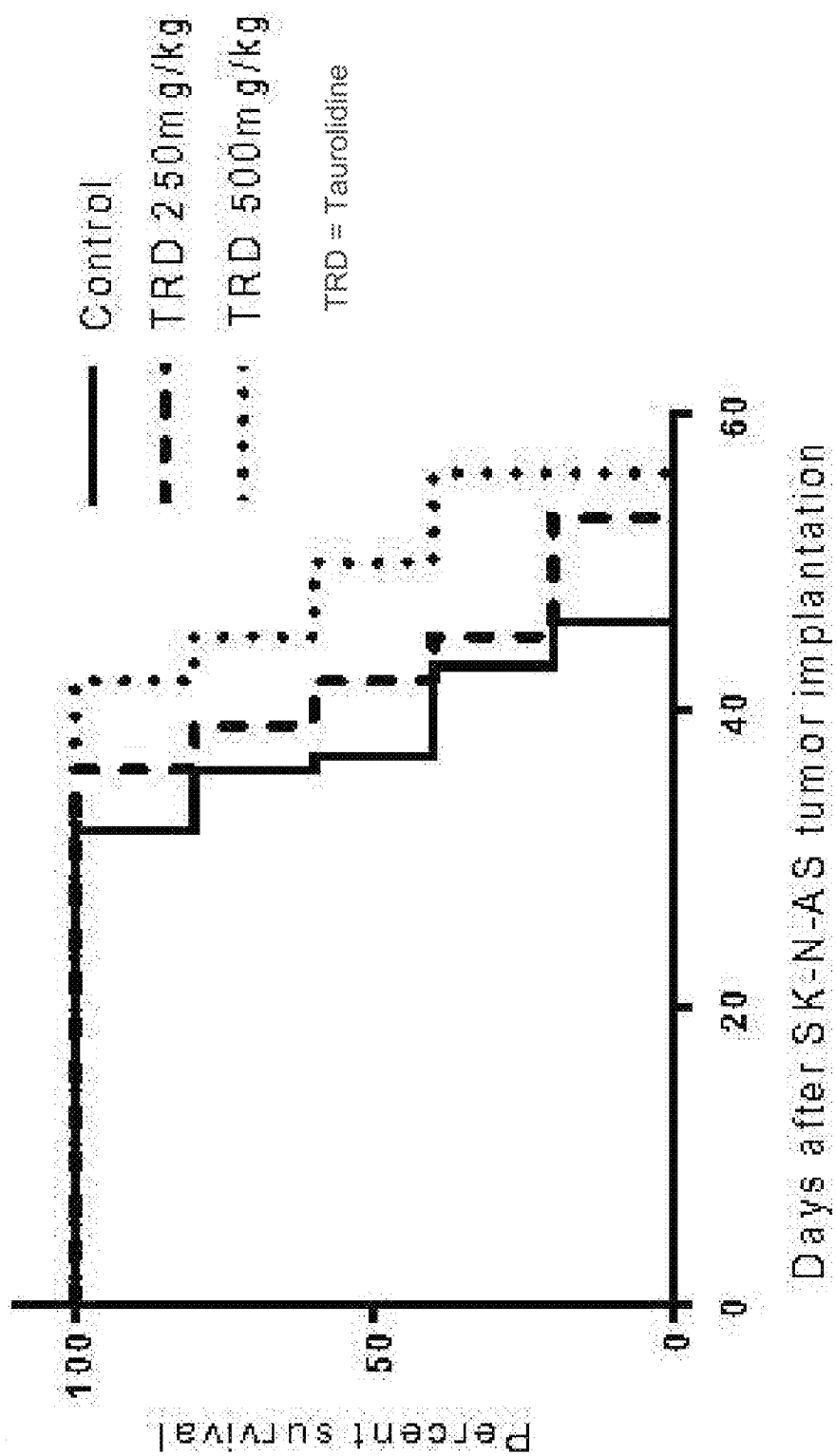

Statistically significant decreases in tumor size were achieved when taurolidine was administered to treat mice with a different cell line (SK-N-AS) also derived from neuroblastoma, though overall survival of the mice implanted with the tumor was not statistically different from the control. See FIGS. 7 and 8.

Figure 9:
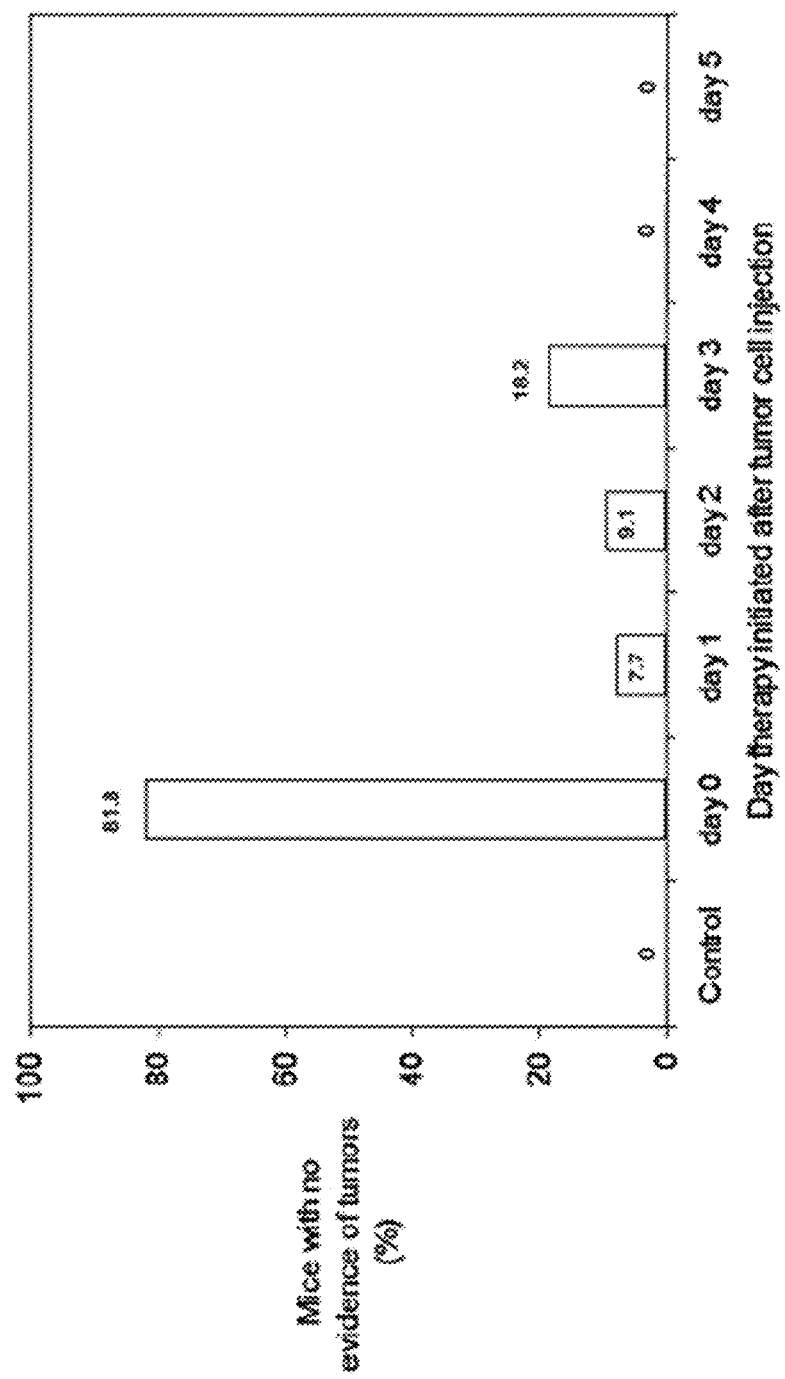
FIG. 9 is a chart showing the effect of delayed administration of a single 3-day i.p. (intraperitoneal) bolus injection regimen of taurolidine (20 mg/mouse/injection) on the occurrence of i.p. human tumor xenografts in female nude mice after the i.p. administration of $5 \times 10^6$ SKOV-3 human ovarian tumor cells.

Taurolidine has also demonstrated efficacy in treating ovarian cancer in a human ovarian cell tumor line implanted in mice. This cell line is known to overexpress C-myc genes. See FIG. 9 which shows the effect of delayed administration of a single 3-day i.p. (intraperitoneal) bolus injection regimen of taurolidine (20 mg/mouse/injection) on the occurrence of i.p. human tumor xenografts in female nude mice after the i.p. administration of $5 \times 10^6$ SKOV-3 human ovarian tumor cells. In this study, taurolidine therapy was initiated on the day of tumor cell inoculation or up to 5 days thereafter. Fourteen days after the final taurolidine injection, mice in all of the groups were sacrificed, and the peritoneal cavity was examined for the presence of tumors. Each experiment was repeated three times, and the pooled number of animals in each group ranged from 15-21 (Cancer Res., 2001 Sep. 15; 61(18):6816-21, Taurolidine: cytotoxic and mechanistic evaluation of a novel antineoplastic agent, Calabresi P1, Goulette F A, Darnowski J W).

And Taurolidine has also demonstrated efficacy in treating lung cancer in a laboratory cell line. This cell line is known to overexpress L-myc genes.

In accordance with the present invention, taurolidine, and/or the hydrolysis products of taurolidine, is/are used to treat tumors that overexpress N-myc genes, C-myc genes and/or L-myc genes in mammalian bodies. Examples of tumors that may overexpress N-myc genes, C-myc genes and/or L-myc genes include, but are not limited to, lymphoma, melanoma, multiple myeloma, neuroblastoma, colon, breast and lung cancers.

Figure 10:
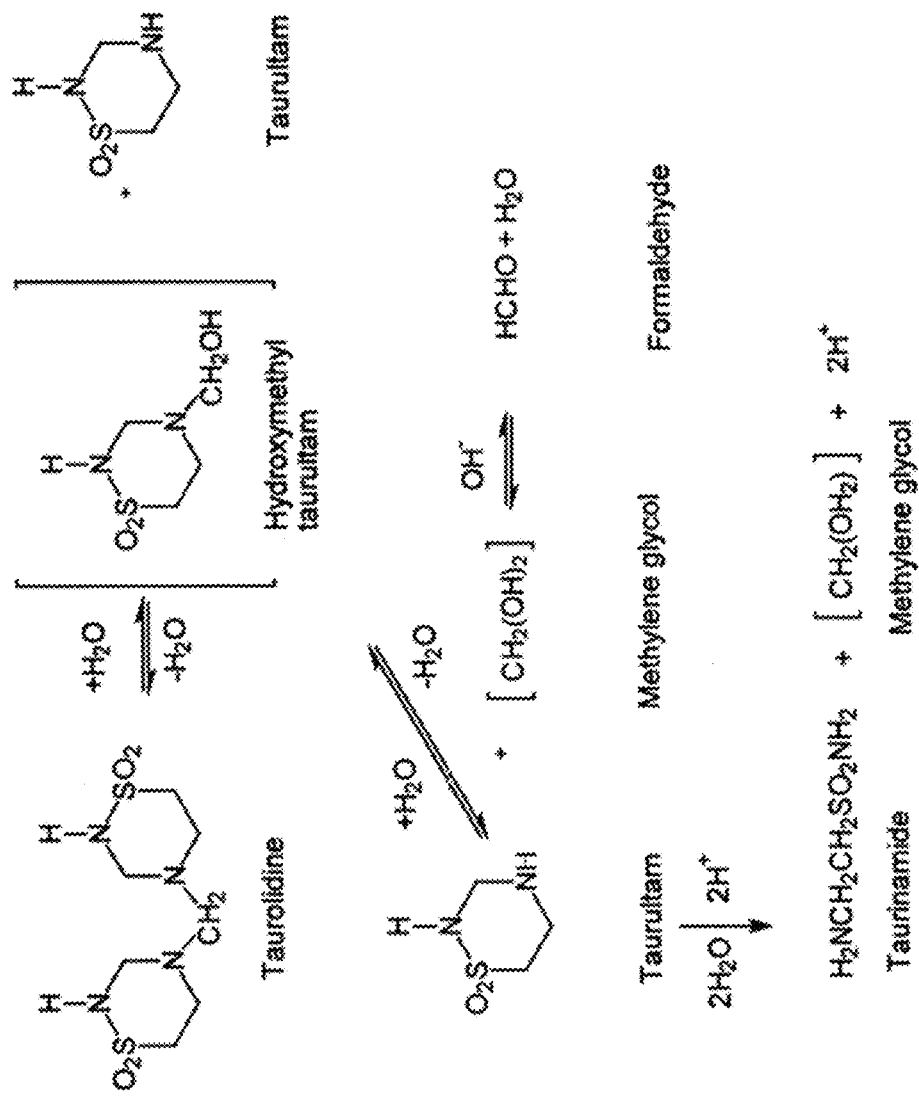
FIG. 10 illustrates the mechanism for the hydrolysis of taurolidine.

The mechanism for the hydrolysis of taurolidine is shown in FIG. 10. The preferred hydrolysis products of taurolidine that may be used to treat tumors that overexpress N-myc genes, C-myc genes and/or L-myc genes in mammalian bodies may comprise at least one from the group consisting of:

taurultam;
taurinamide;
methylene glycol;
taurultam and taurinamide in a ratio of 1 taurultam:7 taurinamide; and
taurultam, taurinamide and methylene glycol in a ratio of 1 taurultam:7 taurinamide:1 methylene glycol.

The taurolidine is given with a dosage range of from 5 mg/kg to 280 mg/kg, with optimal range between 5 mg/kg and 60 mg/kg, from once daily through weekly, for an effective period of time based on individual patient response.

The taurultam is given with a dosage range of from 5 mg/kg to 280 mg/kg, with optimal range between 5 mg/kg and 60 mg/kg, from once daily through weekly, for an effective period of time based on individual patient response. The mean pharmacokinetic parameters of taurultam are shown in FIG. 11.

The taurinamide is given with a dosage range of from 5 mg/kg to 280 mg/kg, with optimal range between 5 mg/kg and 60 mg/kg, from once daily through weekly, for an effective period of time based on individual patient response. The mean pharmacokinetic parameters of taurinamide are shown in FIG. 12.

The methylene glycol is given with a dosage range of from 2.5 mg/kg to 160 mg/kg, with optimal range between 2.5 mg/kg and 30 mg/kg, from once daily through weekly, for an effective period of time based on individual patient response.

The taurultam and taurinamide (in a ratio of 1 taurultam:7 taurinamide) is given with a dosage range of taurultam from 5 mg/kg to 280 mg/kg, with optimal range between 5 mg/kg and 40 mg/kg, combined with taurinamide with a dosage range of from 5 mg/kg to 280 mg/kg, with optimal range from 35 mg/kg to 40 mg/kg, from once daily through weekly, for an effective period of time based on individual patient response.

The taurultam, taurinamide and methylene glycol (in a ratio of 1 taurultam:7 taurinamide:1 methylene glycol) is given with a dosage range of taurultam from 5 mg/kg to 280 mg/kg, with optimal range between 5 mg/kg and 40 mg/kg, from once daily through weekly, combined with taurinamide with a dosage range of from 5 mg/kg to 280 mg/kg, with optimal range from 35 mg/kg to 40 mg/kg, further combined with methylene glycol with a dosage range of from 2.5 mg/kg to 160 mg/kg with optimal range from 5 mg/kg to 40 mg/kg from once daily through weekly, for an effective period of time based on individual patient response.

Dose selection for the hydrolysis products of taurolidine were calculated as follows:

AUC 0-inf Taurultam/AUC 0-inf Taurinamide=42.9/ 312.7=0.14.

Since the molecular weight difference is only a single methyl group, the use of weight-based AUC does not need to be corrected. Therefore the target ratio when giving taurultam and taurinamide in combination is 0.14 or 1:7. And the target ratio when giving taurultam and taurinamide and methylene glycol in combination is 1:7:1.

Effective dosage was computed by computing the human equivalent dosage from the effective mouse dose using the formula:

[Human equivalent dose=mouse mg/kg dose×1 adult human/12 mice×25 child BSA ratio/37 adult BSA ratio=child dose in mg/kg (https://www.fda.gov/downloads/drugs/guidances/ ucm0789 32.pdf)].

The taurolidine, and/or the hydrolysis products of taurolidine, can be given systemically, preferably intramuscularly or intravenously.

In one preferred form of the invention, the taurolidine, and/or the hydrolysis products of taurolidine, is/are delivered systemically in a "shielded form" so that the taurolidine, or the hydrolysis products of taurolidine, can reach the site of the tumor without premature degradation, whereupon the taurolidine, or the hydrolysis products of taurolidine, can treat the tumor.

More particularly, in one preferred form of the invention, the taurolidine, and/or the hydrolysis products of taurolidine, is/are delivered in the form of a nanoparticle, where the nanoparticle comprises a core comprising taurolidine and/or the hydrolysis products of taurolidine, and an exterior coating which is configured to prevent premature exposure of the taurolidine, and/or the hydrolysis products of taurolidine, prior to the arrival of the nanoparticle to the tumor site. The exterior coating breaks down as the nanoparticle travels from the site of insertion to the site of the tumor so as to release the taurolidine, and/or the hydrolysis products of taurolidine, intact at the site of the tumor. In one preferred form of the invention, the coating comprises an absorbable polymer or lipid which breaks down as the nanoparticle travels from the site of insertion to the site of the tumor. By way of example but not limitation, the coating can be created from combinations of copolymers and multimers derived from polymers structured from 1-lactide, glycolide, e-caprolactone, p-dioxanone, and trimethylene carbonate. The coating may also be associated with glycols such as polyethylene glycols (PEGs), which can either be linear or multi-arm structures.

If desired, the nanoparticle may comprise an excipient (e.g., a buffer for providing enhanced hydrolytic stability of the taurolidine and/or hydrolysis product within the nanoparticle).

Additionally, if desired, the nanoparticle can further comprise a coating, wherein the coating is configured to target the nanoparticle to the site of a tumor so as to improve the efficacy of the taurolidine and/or hydrolysis product for treatment of the tumor. In one preferred form of the invention, the coating comprises binding molecules which are configured to target delivery of the nanoparticle to specific tissue.

In another form of the invention, the taurolidine, and/or the hydrolysis products of taurolidine, may be delivered using a polymer system which is configured to delay premature degradation of the taurolidine, and/or the hydrolysis products of taurolidine, and/or to optimize the release properties of the taurolidine, and/or the hydrolysis products of taurolidine. By way of example but not limitation, the taurolidine, and/or the hydrolysis products of taurolidine, may be "pegylated" using polyethylene glycols (PEGs) to delay premature degradation of the taurolidine, and/or the hydrolysis products of taurolidine, and/or to optimize the release properties of the taurolidine, and/or the hydrolysis products of taurolidine.

The taurolidine (and/or the hydrolysis products of taurolidine) may be delivered as either a single agent or in combination with other oncolytic agents and/or radiotherapy. Examples of oncolytic agents that can be combined with taurolidine and/or the hydrolysis products of taurolidine for systemic delivery are platinum compounds (cisplatin, carboplatin), alkylating agents (cyclophosphamide, ifosfamide, melphalan, topoisomerase II inhibitor), vinca alkaloids (vincristine), and topoisomerase I inhibitors (topotecan and irinotecan).

MODIFICATIONS

While the present invention has been described in terms of certain exemplary preferred embodiments, it will be readily understood and appreciated by those skilled in the art that it is not so limited, and that many additions, deletions and modifications may be made to the preferred embodiments discussed above while remaining within the scope of the present invention.

What is claimed is:

1. A method for treating a cancer which overexpresses any of N-myc genes, C-myc genes and/or L-myc genes in a mammalian body in need thereof, the method comprising:
    administering a composition to the mammalian body, wherein the composition consists of taurultam, taurinamide and methylene glycol in a weight ratio of 1 taurultam:7 taurinamide:1 methylene glycol.

2. The method according to claim 1 wherein the dosage range for taurultam is from 5 mg/kg to 280 mg/kg, combined with taurinamide with a dosage range of from 5 mg/kg to 280 mg/kg, combined with methylene glycol with a dosage range of from 2.5 mg/kg to 160 mg/kg, from once daily through weekly, for an effective period of time based on individual patient response.

3. The method according to claim 2 wherein the dosage range for taurultam is from 5 mg/kg to 40 mg/kg, combined with taurinamide with a dosage range of from 35 mg/kg to 40 mg/kg, combined with methylene glycol with a dosage range of from 5 mg/kg to 40 mg/kg, from once daily through weekly, for an effective period of time based on individual patient response.

4. The method according to claim 1 further comprising administering the composition in conjunction with an oncolytic agent and/or radiotherapy.

5. The method according to claim 1 wherein administering the composition comprises delivering to the mammalian body using one from the group consisting of parenteral delivery, intramuscular delivery and intravenous delivery.

6. The method according to claim 1 wherein the composition is included in a nanoparticle, and further wherein the nanoparticle is configured to delay exposure of the composition until the nanoparticle reaches the site of a tumor.

7. The method according to claim 6 wherein the nanoparticle comprises a core of the composition and an exterior coating, wherein the exterior coating is configured to prevent exposure of the composition prior to arrival of the nanoparticle at the site of the tumor.

8. The method according to claim 7 wherein the exterior coating comprises an absorbable polymer or lipid which breaks down as the nanoparticle travels from the site of insertion to the site of the tumor.

9. The method according to claim 1 wherein administering the composition comprises delivering the composition using a polymer system which is configured to delay premature degradation of the composition.

10. The method according to claim 9 comprising pegylating the composition using polyethylene glycols (PEGs) to delay premature degradation of the composition.

* * * * *